(12) United States Patent
Isham (10) Patent No.: US 8,603,129 B2
(45) Date of Patent: *Dec. 10, 2013

(54) RECTAL BALLOON WITH RADIATION SENSOR AND/OR MARKERS

(75) Inventor: John Isham, Houston, TX (US)

(73) Assignee: RadiaDyne, LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/444,626

(22) Filed: Apr. 11, 2012

(65) Prior Publication Data

US 2012/0259197 A1    Oct. 11, 2012

Related U.S. Application Data

(63) Continuation-in-part of application No. 12/141,270, filed on Jun. 18, 2008, now abandoned, which is a continuation-in-part of application No. 12/034,470, filed on Feb. 20, 2008, now Pat. No. 8,080,031, which is a continuation-in-part of application No. 11/933,018, filed on Oct. 31, 2007, now abandoned, which is a continuation-in-part of application No. 11/623,702, filed on Jan. 16, 2007, now abandoned.

(51) Int. Cl.
*A61M 29/00* (2006.01)

(52) U.S. Cl.
USPC ........................................ 606/197

(58) Field of Classification Search
USPC ............... 606/197, 192, 193, 198, 194; 604/96.01, 103.06, 99.01, 99.02, 604/100.01, 100.02, 101.01, 101.02, 604/103.07, 103.08

See application file for complete search history.

(56) References Cited

U.S. PATENT DOCUMENTS

| 5,476,095 | A  | * | 12/1995 | Schnall et al. ........... 600/423 |
| 5,792,070 | A  | * | 8/1998 | Kauphusman et al. ...... 600/549 |
| 6,251,059 | B1 | * | 6/2001 | Apple et al. ............... 600/3 |
| 6,963,771 | B2 |   | 11/2005 | Scarantino |
| 7,361,134 | B2 |   | 4/2008 | Rozenfeld |
| 7,976,497 | B2 |   | 7/2011 | Shah |
| 2003/0028097 | A1 |   | 2/2003 | D'Amico |
| 2006/0017009 | A1 | * | 1/2006 | Rink et al. ............. 250/484.5 |
| 2006/0094923 | A1 |   | 5/2006 | Mate |

OTHER PUBLICATIONS

D'Amico, Anthony V. et al, "A Practical Method to Achieve Prostate Gland Immobilization and Target Verification for Daily Treatment," Int J. Radiation Oncology Biol. Phys., 2001 pp. 1431-1436, vol. 51 No. 5, © 2001 Elsevier Science Inc., U.S.A. (6 pages).

(Continued)

*Primary Examiner* — Ryan Severson
*Assistant Examiner* — Tin Nguyen
(74) *Attorney, Agent, or Firm* — Boulware & Valoir (57) ABSTRACT

A rectal balloon apparatus has a shaft with a fluid passageway extending therethrough. A balloon is affixed over an end of the shaft such that the fluid passageway communicates with an interior of the balloon. The balloon has a laterally flat surface thereon when inflated. The laterally flat surface of the balloon has a longitudinal groove formed thereon. The balloon has a radiation sensor positioned within the groove and a plurality of fiducial markers positioned on a surface of the balloon. A stopper is slidably mounted on the shaft.

9 Claims, 5 Drawing Sheets

(56) References Cited

OTHER PUBLICATIONS

D'Amico, Anthony V. et al, "A Prospective Evaluation of Rectal Bleeding After Dose-Escalated Three-Dimensional Conformal Radiation Therapy Using an Intrarectal Balloon for Prostate Gland Localization and Immobilization," 2005,—Journal Urology, pp. 780-784, vol. 67, No. 4, © 2006 Elsevier Inc. (5 pages).

Little, Darren J. et al., Use of Portal Images and BAT Ultrasonography to Measure Setup Error and Organ Motion for Prostate IMRT: Implications for Treatment Margins, Int'l J. Radiation Oncology Biol. Phys., 2003, pp. 1218-1224, vol. 56, No. 5 © 2003 Elsevier Inc. (7 pages).

McGary, John E. et al., Prostate Immobilization Using a Rectal Balloon,—Journal of Applied Clinical Medical Physics, 2002, pp. 6-11, vol. 3, No. 1, © 2002 Am. Coll. Med. Phys. (6 pages).

Patel, Rakesh R et al., "Rectal Dose Sparing with a Balloon Catheter and Ultrasound Localization in Conformal Radiation Therapy for Prostate Cancer," Radiotherapy & Oncology Journal of the European Society for Therapeutic Radiology and Oncology, 2003, pp. 285-294, vol. 67, © 2003 Elsevier Science Ireland Ltd. (10 pages).

Van Lin, Emile N. J. TH. et al., "Rectal Wall Sparing Effect of Three Different Endorectal Balloons in 3D Conformal and IMRT Prostate Radiotherapy," Int'l J. Radiation Oncology Bioi. Phys., 2005, pp. 565-576, vol. 63, No. 2 © 2005 Elsevier, Inc. (12 pages).

Poli, M. Esmeralda Ramos et al., An Assessment of PTV Margin Definitions for Patients Undergoing Conformal 3D External Beam Radiation Therapy for Prostate Cancer Based on an Analysis of 10,327 Pretreatment Daily Ultrasound Localizations, Int. J. Radiation Oncology Bioi. Phys., 2007, pp. 1430-1437, vol. 67, No. 5, ©Elsevier Inc. (8 pages).

Pollack, Alan et al., "Prostate Cancer Radiation Dose Response: Results of the M.D. Anderson Phase III Randomized Trial," Int. J. of Radiation Oncology Bioi. Phys., 2002, pp. 1097-1105. vol. 53, No. 5, © 2002 Elsevier Science Inc. (9 pages).

Storey, Mark R et al., "Complications from Radiotherapy Dose Escalation in Prostate Cancer: Preliminary Results 1 of a Randomized Trial," Int. J. Radiation Oncology Bioi. Phys., 2000, pp. 635-642. vol. 48, No. 3, © 2000 Elsevier Science Inc. (8 pages).

Van Lin, Emile N.J. TH. et al., "Reduced Late Rectal Mucosal Changes After Prostate Three-Dimensional Conformal Radiotherapy with Endorectal Balloon as Observed in Repeated Endoscopy," Int. J. Radiation Oncology Biol. Phys., 2007, pp. 799-811, vol. 67, No. 3, © 2007 Elsevier Inc. (13 pages).

Wang, Zhou et al., "The Effect of Positional Realignment on Dose Delivery to the Prostate and Organs-at-Risk for 3DCRT," Medical Dosimetry, 2007, pp. 1-6, vol. 32, No. 1, © 2007 American Association of Medical Dosimetry (6 pages).

Zietman, A. L et al., "A Randomized Trial Comparing Conventional Dose (70.2 GyE) and High-Dose (79.2 GyE) Conformal Radiation in Early Stage Adenocarcinoma of the Prostate; Results of an Interim Analysis of RROG 45-09" Int. J. Radiation Oncology Biol. Phys., 2004, pp. S131-S132, vol. 60, No. 1, Supp. 2004, © 2004 Elsevier B. V. (2 pages).

* cited by examiner

RECTAL BALLOON WITH RADIATION SENSOR AND/OR MARKERS

PRIOR RELATED APPLICATIONS

The present application is a continuation-in-part (CIP) of U.S. Ser. No. 12/141,270, filed on Jun. 18, 2008, presently pending, which is a CIP of U.S. Ser. No. 12/034,470, filed on Feb. 20, 2008, now patented as U.S. Pat. No. 8,080,031, which is CIP of U.S. Ser. No. 11/933,018, filed on Oct. 31, 2007, abandoned, which is a CIP of U.S. Ser. No. 11/623,702, filed on Jan. 16, 2007, abandoned, and all of which are incorporated by reference herein in their entirety.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

FIELD OF THE INVENTION

The present invention relates to an apparatus for facilitating performance of diagnostic and therapeutic treatment of disease. Particularly, the present invention relates to rectal balloons that are used for immobilizing the region surrounding the prostate during pre-treatment simulation and target localization, as well as during the delivery of radiation therapy to treat prostate cancer. More particularly, the present invention relates to minimally invasive rectal probes.

BACKGROUND OF THE INVENTION

Treatment of prostate cancer using radiation therapy is difficult due to the prostate's position near radiation-sensitive tissues, and is further complicated by prostate motion. Adenocarcinoma of the prostate commonly occurs in the posterior portion of the prostate gland, which is in very close proximity to the rectal wall. To date, external beam radiation treatment, urethrograms, CT scans and magnetic resonance imaging (MRI) have all been used to visually localize the prostate, as well as the normal critical structures in the surrounding area.

U.S. Pat. No. 5,476,095, issued on Dec. 19, 1995 to Schnall et al., describes an insertable pickup probe for use in providing diagnostic MRI images. The pickup probe, in its preferred embodiment, is for use in imaging the male prostate and comprises an elongated shaft supporting an inflatable patient interface balloon at its distal end. The interface balloon comprises an inner balloon and an outer balloon, between which a receiving coil is positioned. A lumen for air supply is provided in the shaft for expanding the inner balloon against the outer balloon to place the receiving coil in close proximity to the area of interest in order to provide MRI images.

Typically, the planning of radiation therapy for the treatment of prostate cancer involves the patient undergoing a CT-based simulation scan of the pelvis to determine the location of the prostate gland. In the simulation phase, the patient is placed on CT equipment that is preferably similar to the radiation treatment equipment (except that it does not generate the high energy radiation beam). The simulation equipment is positioned to simulate the delivery of the sequence of treatment beams prescribed by the treating oncologist. Normally, during the simulation procedure, CT images are acquired. These CT images allow the oncologist to locate the position of the tumor and help to facilitate the composition of a radiation treatment plan. This treatment plan delineates the positions of the radiation equipment components for delivery of the treatment beams.

During the actual treatment phase, the patient is placed in the same position on the treatment equipment as in the simulation scans. Radiation-emitting devices are generally known and used for radiation therapy in the treatment of patients. Typically, a radiation therapy device includes a gantry, which can be swiveled around a horizontal axis of rotation in the course of a therapeutic treatment. A linear accelerator is located in the gantry for generating a high-energy radiation beam for therapy. During treatment, the radiation beam is provided by this equipment and is delivered to the patient at the precise location as delineated by the physician during simulation. A further feature of radiation therapy involves portal images, which are commonly used in radiation therapy to verify and record the patient tumor location. Portal images include manual (film) and electronic images (EPI) taken before and/or after the treatment.

During external beam radiation therapy, radiation is directed to the target prostate, which is near the rectal wall. A misdirected radiation beam may perforate the rectal wall causing radiation proctitus (rectal bleeding). This toxicity is related to the total radiation dose prescribed and the volume of the anterior rectal wall receiving a high radiation dose. A major factor limiting radiation oncologists' attempts to reduce the volume of the anterior rectal wall receiving a high radiation dose is the position of the prostate gland as well as the intrinsic motion up to 5 mm in the anterior to posterior direction caused by rectal peristalsis. Accordingly, oncologists generally will add a margin to the radiation field in order to ensure that the entire prostate gland receives the prescription dose. This margin is typically on the order of 5 to 15 mm. As a consequence, lower doses of radiation may need to be used so as not to overexpose radiation sensitive structures. However, this may lead to inadequate radiation treatment and a higher probability of local cancer recurrence.

U.S. Patent Publication No. 2003/0028097, published on Feb. 6, 2003 to D'Amico et al., describes an immobolizer probe system and method. This system has an insertable probe for immobilizing a region of interest during staging and radiation therapy thereof. In particular, this device uses a balloon having a rectangular cross section connected to a shaft. The shaft extends to an end of the balloon so as to allow fluid flow through an interior of the shaft and into the balloon so as to selectively inflate the balloon once the balloon is installed into the rectal cavity. The balloon, shaft and handle are bonded together so that they move radially as a single unit when torque is applied. A syringe is provided which connects the shaft and serves as an air pump to deliver a volume-limited amount of air to the air lumen of the shaft to the balloon. A stop cock is provided to maintain the air within the balloon.

One of the problems with the subject of U.S. Patent Publication No. 2003/0028097 is the discomfort associated with installing the rectal balloon within the rectal cavity. In particular, a relatively sturdy and wide diameter shaft is connected to a relatively large thick-walled balloon. Because the balloon is not supported by anything other than by the shaft, the balloon is formed of a relatively rugged and thick material. Because of the relatively large size of the shaft and the thick material of the rectangular-cross section balloon, the installation of the rectal balloon creates a large amount of discomfort for a patient. It is often difficult for the medical personnel to know exactly how far within the rectum the balloon has been installed. It is difficult to achieve a standardized and fixed position of the balloon during each and every use. The medical personnel must generally approximate the desired position of the balloon within the rectal cavity. As such, a need has developed whereby the rectal balloon can be formed of a minimal diameter shaft and of a balloon of relatively thin material.

A second problem with the rectal balloon of U.S. Patent Publication No. 2003/0028097 is that it is "non-conforming" and when squeezed, the shape of the balloon is lost, because there are no interior welds restraining the balloon. Thus, even if shaped when lightly inflated, the shape is lost when squeezed and the balloon bulges wherever it is not squeezed, thus allowing the prostate to slide off its surface. As such, a need developed to provide a rectal balloon that retains the prostate in a proper seated position when the balloon is in a fully inflated or squeezed condition. A balloon that can retain a shape, even when squeezed is known as a "conforming" balloon.

The inventor is also the owner of U.S. Ser. No. 11/623,702 ("the '702 application"), filed on Jan. 16, 2007, and U.S. Ser. No. 11/933,018 ("the '018 application), filed on Oct. 31, 2007. The '018 application is a continuation-in-part of the '702 application. Each of these applications describes a rectal balloon apparatus similar to that of the present invention. Both the '702 and the '018 applications describe a sleeve positioned over the balloon when the balloon is in the uninflated condition. The sleeve maintains the balloon in a tightly juxtaposed position against the shaft for a minimal profile for insertion into the rectum. Additionally, the '018 application describes the sleeve as having a frangible seam such that it can be torn away as it is pulled away from the balloon.

Experimentation also showed that the shape of the surface of the balloon that engages the prostate is of great importance. The '702 application contemplates a seating area for the prostate to be positioned on. The '018 application describes two different inflated conditions of the balloon, each with a unique shape. In the first inflated condition, the balloon has a laterally flat seating area on which the prostate rests. When additional fluid is added to the balloon, it moves to the second inflated condition. In the second inflated condition, the balloon has a laterally flat seating area and a bulbous portion formed at the end of the balloon adjacent to the tip. The bulbous portion works against the natural forces seeking to expel the balloon from the rectum. The location of this bulge serves to contour the seminal vesicles in proper alignment.

U.S. Ser. No. 12/034,470, now U.S. Pat. No. 8,080,031, describes and claims a conforming balloon, wherein an interior weld restrains the balloon such that it is a does not lose shape, even when squeezed in the highly mobile environment of the rectum. In more detail, the balloon is made of three layers, wherein the middle layer is connected to the top layer, to provide a central groove which provides the dimpled seating area into which the prostate is wedged. The weld is shifted distally slightly, so that there is a bit more material proximal to the weld, which when hyperinflated stretches more, providing a proximal bulge, serving to further wedge the seminal vesicles into place.

As discussed above, a very important consideration when treating patients using radiation therapy is that the proper dose of radiation reaches the treatment site. This is very important whether the treatment method utilizes implanted radiation seeds or external beams of radiation. Excessive dosing of the patient can lead to severe side effects including impotence and urinary incontinence. A proper treatment plan should deliver an adequate amount of radiation to the treatment site while minimizing the dose delivered to the surrounding tissues.

U.S. Pat. No. 6,963,771, issued on Nov. 8, 2005 to Scarantino et al., describes a method, system and implantable device for radiation dose verification. The method includes (a) placing at least one wireless implantable sensor in a first subject at a target location; (b) administering a first dose of radiation therapy into the first subject; (c) obtaining radiation data from the at least one wireless implantable sensor; and (d) calculating a radiation dose amount received by the first subject at the target location based on the radiation data obtained from the at least one wireless sensor during and/or after exposure to the first administered dose of radiation to determine and/or verify a dose amount of radiation delivered to the target location.

U.S. Pat. No. 7,361,134, issued on Apr. 22, 2008 to Rozenfeld et al., teaches a method of determining the dose rate of a radiation source including locating three or more detectors in the vicinity of a source. Each of the detectors provides an output indicative of the amount of radiation received from the source and determines the location of the source from at least some of the detector outputs.

It is an object of the present invention to provide a rectal balloon apparatus, which is easy to use and easy to install.

It is another object of the present invention to provide a rectal balloon apparatus, whereby the position of the balloon can be easily ascertained by a medical personnel.

It is a further object of the present invention to provide a rectal balloon apparatus, which maximizes the comfort of the patient.

It is a further object of the present invention to provide a rectal balloon apparatus, which has improved holding stability when inflated.

It is a further object of the present invention to provide a rectal balloon apparatus, which has a flexible shaft.

It is another object of the present invention to provide a rectal balloon apparatus, which enhances the ability to properly seat the prostate on a flat surface of the rectal balloon.

It is a further object of the present invention to provide a rectal balloon apparatus, which avoids potential allergic reactions.

It is still a further object of the present invention to provide a rectal balloon apparatus, which is easy to manufacture and relatively inexpensive.

It is still another object of the present invention to provide a rectal balloon apparatus, which uniformly displaces the anal verge.

It is a further object of the present invention to provide a rectal balloon apparatus that facilitates the removal of fluid from the interior of the balloon.

It is a further object of the present invention to provide a rectal balloon apparatus that provides a visual indication of when the balloon is positioned beyond the anal verge.

It is still a further object of the present invention to provide a rectal balloon apparatus that can be placed in the same position during successive treatments.

It is another object of the present invention to provide a rectal balloon apparatus that senses the amount of radiation being received at a treatment site.

It is a further object of the present invention to provide a rectal balloon apparatus that can provide a clear image of the anterior and posterior walls of the rectum.

These and other objects and advantages of the present invention will become apparent from a reading of the attached specification and appended claims.

BRIEF SUMMARY OF THE INVENTION

The present invention is a rectal balloon apparatus that comprises a shaft having a fluid passageway extending therethrough and with indicia formed on an exterior of the shaft. The shaft has a stopping means that is slidably longitudinally along the shaft so as to reside at a desired indicia and which fixes the amount of movement of the shaft into the rectum. A balloon is affixed over an end of the shaft such that the fluid passageway communicates with an interior of the balloon. The balloon is movable from a non-inflated condition to an inflated condition. The balloon has a sensing means affixed on it, which senses the amount of radiation delivered to the sensing means. The balloon has a generally laterally flat surface when in the inflated condition and there is a longitudinal groove formed in the laterally flat surface.

In the present invention, the sensing means is affixed within the groove. A plurality of fiducial markers are formed on a surface of the balloon. The fiducial markers are affixed or formed on different surfaces of the balloon. One plurality of fiducial markers may be positioned on one side of the groove and a second set may be positioned on an opposite side of the groove. One set of fiducial markers may be positioned on the top surface of the balloon and a second set of fiducial markers may be placed on the bottom surface of the balloon. The stopping means may be a semispherical member that is slidably mounted on the shaft, which has a curved surface facing the balloon.

In more detail, the invention is a prostate immobilizing rectal balloon, said rectal balloon comprising: a flexible shaft having a fluid passageway extending therethrough and having a distal end and a proximal end; a balloon having an upper surface, a bottom surface, a distal end near said distal end of said shaft and an proximal end that is affixed to the proximal end of said shaft, such that said fluid passageway communicates with an interior of said balloon. The balloon comprises a top layer connected to a bottom layer to form said balloon, and also a middle layer extending between said top layer and said bottom layer, wherein said middle layer is connected to said top layer at a groove overlying said shaft. The balloon will have a non-inflated condition, and an inflated condition wherein said upper surface is generally laterally flat and said bottom surface is rounded, said groove having depth and forming a central seating area that is configured to engage with a prostate. The balloon also has a second further inflated condition wherein said upper surface has a bulge at said distal end of said balloon, wherein said bulge immobilizes said prostate in position at said groove. The balloon also has a radiation sensor in said groove for determining radiation dose from an external beam radiation device, or a plurality of fiducial markers on said balloon for imaging said balloon when in use, or both.

DETAILED DESCRIPTION OF THE INVENTION

Figure 1:
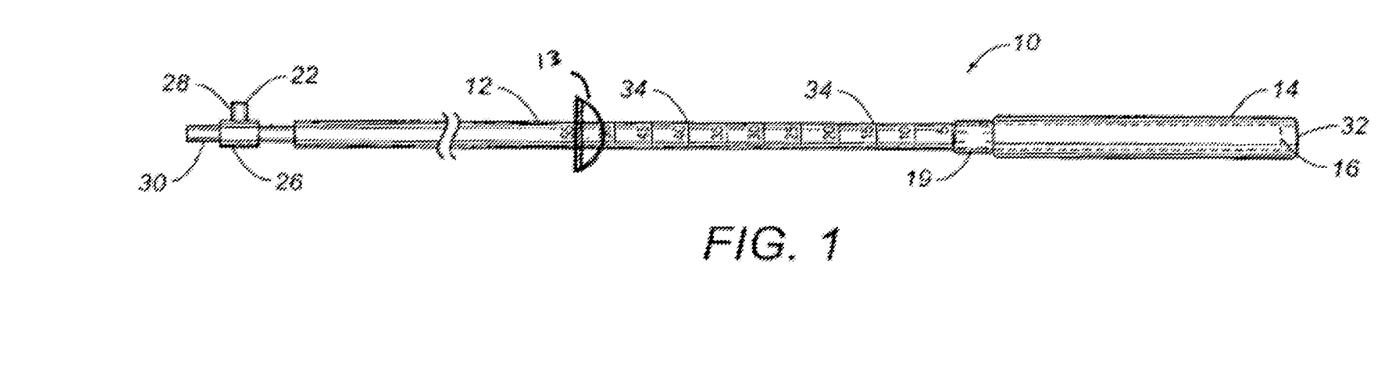
FIG. 1 is a side elevational view, partially transparent, which shows the rectal balloon apparatus in an uninflated condition.

Referring to FIG. 1, there is shown the rectal balloon apparatus 10 in accordance with the preferred embodiment of the present invention. The rectal balloon apparatus 10 includes a shaft 12 having a fluid passageway extending therethrough. A balloon 14 is affixed over the end 16 of the shaft 12. The balloon 14 is shown in an uninflated condition. The fluid passageway of the shaft 12 can communicate with the interior of the balloon 14. Also shown is the stopper 13, which is slidable along the shaft 12. The stopper 13 has a hemispherical shape. The stopper 13 serves to assure uniformity in the positioning of the balloon 14 during radiation therapy.

The shaft 12 is a generally longitudinal shaft, which has the fluid passageway extending through the center thereof. The shaft 12 is made of a flexible material. A valve assembly 22 is affixed to the shaft 12 opposite the balloon 14. The valve assembly 22 can have a variety of configurations. FIG. 1 illustrates the valve assembly 22 as an inline valve assembly configuration. The valve assembly 22 may also be an angled valve assembly configuration. The valve assembly 22 includes a stopcock 26. A valve 28 facilitates the ability of the stopcock 26 to open and close so as to selectively allow the fluid to pass into the shaft 12. A port 30 allows the valve assembly 22 to be connected to a supply of the fluid. When the stopcock 26 is opened by the rotation of the valve 28, the fluid will flow through the valve assembly 22, through the interior passageway of the shaft 12 and into the interior of the balloon 14. The valve 28 can then be closed so as to maintain the inflated configuration of the balloon 14. When the procedure is finished and the fluid needs to be removed from the balloon 14, the valve 28 of stopcock 26 can then be opened so as to allow for the release of fluid therethrough.

The opposite end 16 of the shaft 12 contacts the end 32 of the balloon 14. The end 16 is suitably curved or dome-shaped so as to allow the shaft 12 to facilitate the introduction of the balloon 14 into the rectal cavity. The shaft 12 has indicia 34 formed therealong. It can be seen that the indicia 34 has numerical references associated therewith. These numerical references are indicative of the distance that the balloon 14 has been inserted into the rectum. As such, the indicia 34 provide a clear indication to the medical personnel of the desired location of the rectal balloon 14. Here, the stopper is shown positioned at indicia 34 number "55."

A ring 19 is affixed to the shaft 12 adjacent to the balloon 14. This ring 19 can be of a bright color, such as blue, so as to provide the medical personnel with positive indication of when the balloon 14 is past the anal verge. The ring 19 is approximately 5 millimeters long. The stopper 13 is shown as positioned away from the balloon 14. This would be the position prior to insertion. The stopper 13 is slidably mounted on the shaft 12. The stopper 13 has a semi-spherical shape so as to conform to the entrance of the rectum. A suitable locking mechanism can be provided so as to fix the stopper at a desired location.

Figure 2:
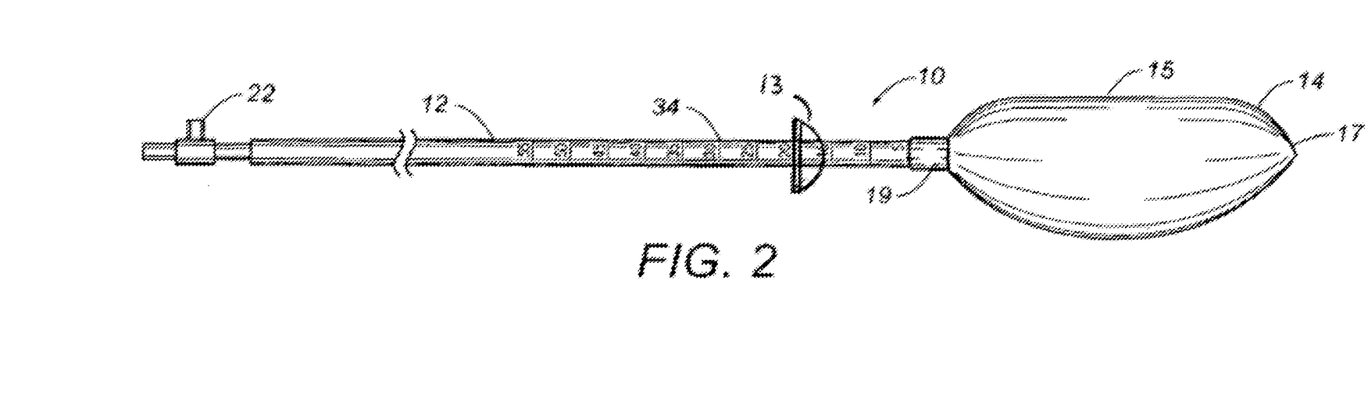
FIG. 2 is a side elevational view of the rectal balloon apparatus of the present invention in an inflated condition.

FIG. 2 illustrates an isolated view of the apparatus 10 after being installed within the rectum. The fluid can be introduced through the valve assembly 22 and through the interior passageway of the shaft 12 so as to inflate the balloon 14. The ring 19 is shown as adjacent an end of the balloon 14. The balloon 14 has a seating area 15 so that the prostate can be properly positioned thereon. The balloon 14 has a head portion 17 adjacent the tip of the balloon 14 opposite the shaft 12. When the balloon 14 is installed and inflated, the prostate will reside on the flat surface 15 in a seated position. The head portion 17 will abut the tip of the prostate.

After the procedure has been completed, the balloon 14 can be deflated and easily pulled outwardly of the rectum in its deflated condition. In FIG. 2, it can be seen that the stopper 13 has been moved along the shaft 12 (from its position in FIG. 1) to indicia 34, specifically at the number "20." This serves to assure that the balloon 14 will be in a proper position during subsequent radiation treatments.

Figure 3:
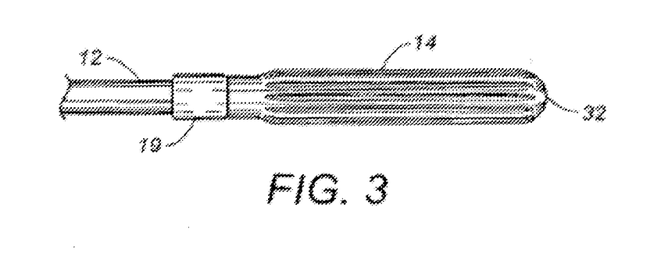
FIG. 3 is an isolated view showing the compact folding of the balloon over the end of the shaft.

FIG. 3 shows that the balloon 14 is neatly folded and compressed over the outer diameter of the shaft 12. The shaft 12 will have a rounded end abutting the end 32 of the balloon 14. As such, a comfortable rounded profile is provided at this end 32. The end 32 of the balloon 14 is sealed over the outer diameter of the shaft 12. The balloon 14 is pre-vacuumed during production to produce a minimal profile during use. The ring 19 is placed over the shaft 12.

Figure 4:
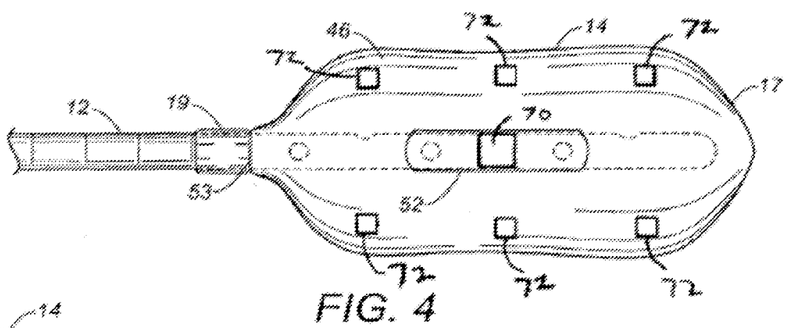
FIG. 4 is a top view of the inflated balloon as used in the rectal balloon apparatus of the present invention showing, in particular, the application of fiducial markers to a surface of the balloon and a sensor in the groove.

FIG. 4 is a top view of the balloon 14 from the side of the balloon 14, which engages with the prostate. Central seating area 46 is shown as having a groove 52 formed thereon. The groove 52 is generally rectangularly-shaped and engages with the tip of the prostate, reducing lateral motion. The central seating area 46 and the groove 52 greatly enhance the holding stability of the balloon 14 of the present invention. In FIG. 4, it can also be seen that head portion 17 of the balloon 14 is generally V-shaped. This shape makes insertion of the balloon 14 into the rectum easier for medical personnel and more comfortable for the patient. The balloon 14 has a thermally welded bond 53 connecting it to the shaft 12.

Importantly, in FIG. 4 it can be seen that a sensor 70 is located within the groove 52 of the central seating area 46. The sensor 70 allows the treating physician to determine the dose of radiation being received at the treatment area when the balloon 14 is in place. The sensor 70 is located in the middle of the groove 52. This location is ideally centrally located on the prostate when the balloon 14 is in place. By positioning the sensor 70 adjacent the prostate, an accurate measurement of the radiation delivered to the prostate is achieved.

The sensor 70 can be chosen from any of the available implantable sensors that enable to user to monitor the radiation dosage for external beam radiation therapy devices. A particularly preferred sensor is the sensor described in 61/481,503, filed May 2, 2011, and the utility filing related thereto Ser. No. 13/444,584, filed Apr. 11, 2012, and expressly incorporated by reference herein. That sensor is a plastic scintillator detector cable comprising a single, short length of scintillator fiber operably coupled to a suitable length of optic fiber, which has a standard data coupler or connector at the end of the cable opposite the scintillator fiber. The scintillator detector is thus at the distal end of the cable and a suitable data coupler is at the proximal end, and the entirety of the cable is enclosed in a flexible, opaque covering (e.g., the typical wire jacket).

In another embodiment, the cable has at least two separate, but closely juxtaposed, plastic scintillator detectors. The two detectors are parallel, but offset from one another in the longitudinal axis, so that radiation can be simultaneous assessed at two ends of a target, such as on either end of the prostrate or both ends of an irradiated throat area, and the like.

In preferred embodiments, this sensor cable is contained in the layer between the upper and middle layers of the balloon, thus being protected from the environment and immediately adjacent the prostate, and the distal end of the cable affixed to at least a portion of the shaft such that the connectors extend outside the body cavity and can be plugged into the appropriate device (e.g., a scintillation counter).

FIG. 4 also shows a plurality of fiducial markers 72 located on or below the surface of the balloon 14. The fiducial markers 72 may be made of a tungsten material or any of the known radiopaque or reflective materials, depending on the imaging means used. Our experimentation has shown that through the use of these fiducial markers 72 on the balloon 14, a treating physician can get a very clear image of the anterior and posterior walls of the rectum. In FIG. 4, it can be seen that the fiducial markers 72 are positioned in spaced relation to each other on the top surface of the balloon 14. Three of the fiducial markers 72 are positioned in linear alignment on one side of the groove 52. Another three fiducial markers 72 are arranged on the opposite side of the groove 52.

A further benefit can be realized by utilizing an additional fiducial marker in the form of a radioactive seed implanted or injected into the prostate. The radioactive seed combined with the fiducial markers 72 allows for triangulation to make certain that the balloon is in the correct position for treatment.

Additional benefit can be realized if the fiducial marker is contained on or within the cable. For example, the fiducial marker can be at the tip or on the surface of the cable, and in fact, the fiducial marker can be positioned inside the cap designed in Ser. No. 13/444,584. It could also be placed on or inside the tip of the balloon shaft.

Figure 5:
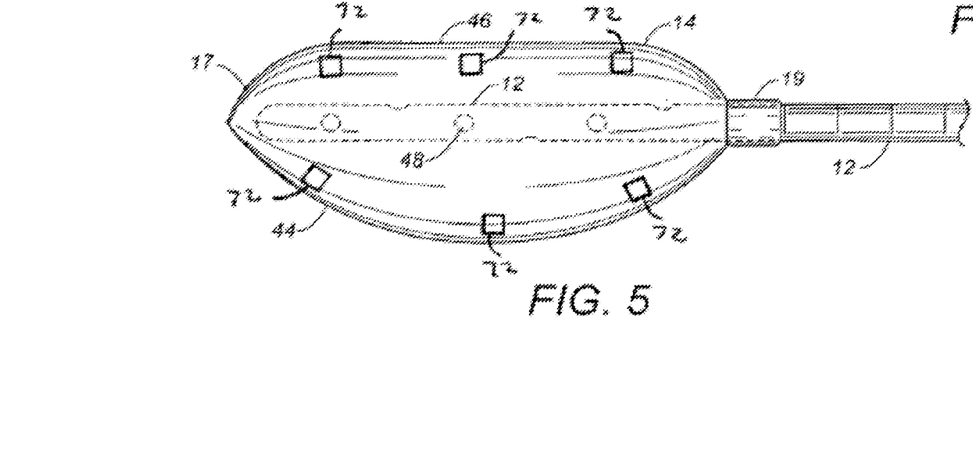
FIG. 5 is a side view, partially transparent, of the balloon of the rectal balloon apparatus in a first inflated condition.

FIG. 5 is an isolated view of the balloon 14 as inflated to a first inflated condition. In this condition, the balloon 14 has a central seating portion 46, a head portion 17 and a bottom portion 44. When inflated, the central seating area 46 has a lateral flatness for the prostate to rest upon. The lateral flatness of the seating area 46 (together with groove 52) will prevent the prostate from sliding to one side or the other. The bottom portion 44 is rounded and contacts the rectal wall. The head portion 17 is generally V-shaped so as to facilitate easier insertion of the balloon 14. The material of the balloon 14 is formed of a non-latex material so as to avoid allergic reactions. The shaft 12 is shown extending into the interior of the balloon 12.

A plurality of holes 48 are formed in the shaft 12 through which the balloon 14 is filled with fluid. The plurality of holes 48 are formed within the balloon 14 so as to allow fluid to be introduced into and removed from the balloon 14. It can be seem that each of the holes 48 is spaced from and offset by 90° from an adjacent hole around the diameter of shaft 12. A total of six holes are formed in the shaft 12 within balloon 14 so as to allow the fluid to pass from an interior of shaft 12 to the interior of the balloon 14. This arrangement of holes 48 facilitates complete extraction of the fluid from the balloon 14. Under certain circumstances, one of the holes may become clogged or blocked by contact between the body and the balloon, the staggered arrangement of holes assures that the unblocked holes 48 allow the fluid to continue to be easily extracted.

In FIG. 5, it can be seen that additional fiducial markers 72 are positioned on the opposite side of balloon 14. The fiducial markers 72 are generally arranged symmetrically on opposite sides of the balloon 14.

Figure 6:
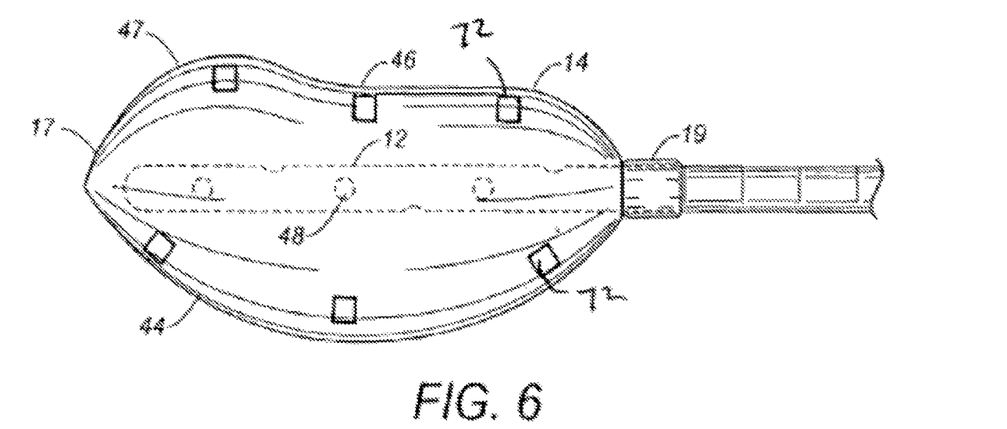
FIG. 6 is a side view, partially transparent, of the balloon of the rectal balloon apparatus in the second inflated condition.

FIG. 6 is an isolated view of the balloon 14 as inflated to a second (more) inflated condition. In the second inflated condition, the balloon 14 has a first bulge 47 formed at the head portion 17 (proximal end). The balloon also has a laterally flat seating portion 46. The first bulge 47 can be utilized in certain conditions to better isolate the prostate. Generally, the first bulge 47 will be introduced when at least 110 cc of fluid are introduced into the balloon 14, so as to slightly overinflate the balloon.

Figure 7:
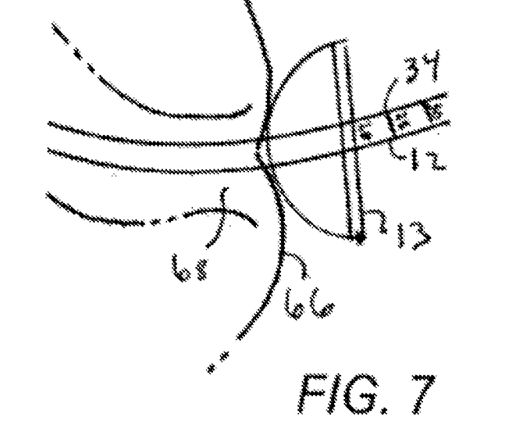
FIG. 7 is a view of the operation of the stopper of the rectal balloon apparatus.

FIG. 7 shows an isolated view showing the stopper means 13 when the balloon 14 has been inserted into the patient's rectum. The stopper means 13 has been moved along the shaft 12 up against the patient's buttocks 66 and adjacent the anus, without having entered the anal canal 68. It can be seen that the stopper means 13 is positioned such that it resides along indicia 34 number "20." Thus, during a first treatment, a treating physician would place the balloon 14 in the proper position and then slide the stopper means 13 up against the patient's buttocks 66. The physician would then make note of the position of the stopper means 13. Then, during subsequent treatments, it would be easier for the physician to place the balloon 14 properly. The physician would simply have to insert the balloon 14 and shaft 12 to the extent necessary such that the stopper means 13 would rest at the same indicia 34 as during the previous treatment when the stopper means 13 is pushed up against the patient's buttocks 66. The stopper means may be shaped in a variety of ways, but it is shown here to have an arcuate front surface to conform to a patient's anatomy.

Figure 8:
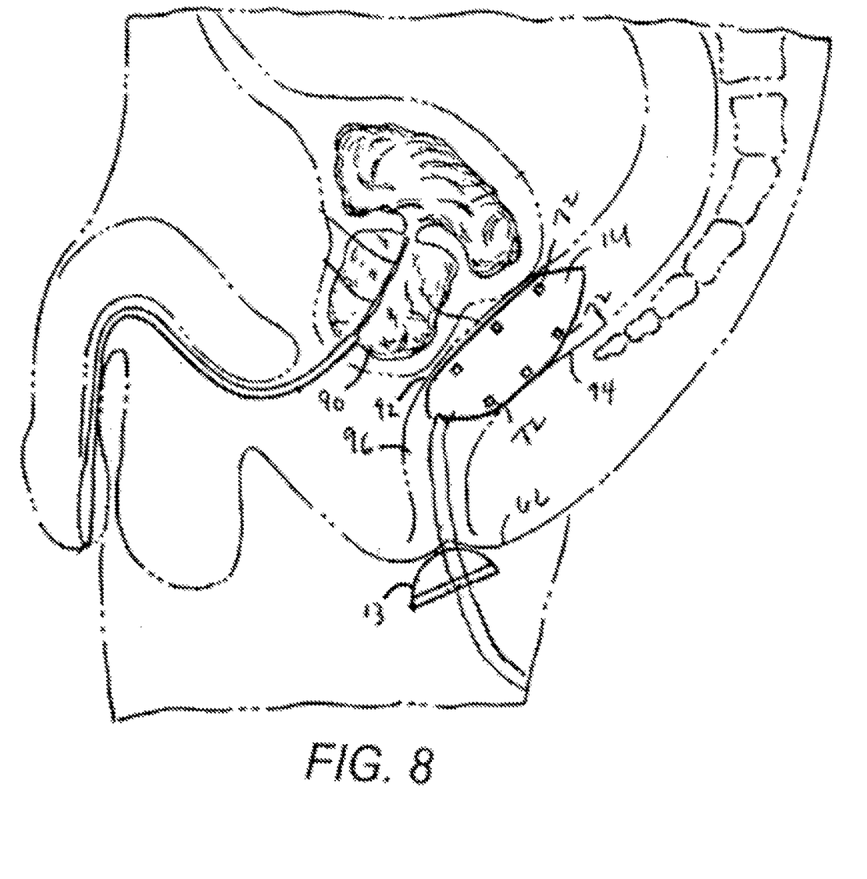
FIG. 8 is side view of the balloon of the rectal balloon apparatus positioned within the rectum and in an inflated condition.

FIG. 8 shows an anatomical side view of the rectal balloon apparatus 10 positioned within a patient's rectum. The balloon 14 is shown in an inflated condition and positioned up against and between the anterior wall 92 and the posterior wall 94 of the rectum 96. It can be seen that the balloon 14 is positioned adjacent the prostate 90. Additionally, it can be seen that the plurality of fiducial markers 72 are generally positioned adjacent either the anterior wall 92 or the posterior wall 94 of the rectum 96. Thus, when a treating physician can determine the position of the plurality of fiducial markers 72, he or she may obtain a clear image of the contours of the anterior wall 92 and the posterior wall 94 of the rectum 96 by essentially "connecting the dots." FIG. 8 also shows the importance of the flexible aspect of the shaft 12 and the utilization of the stopper means 13.

Figure 9:
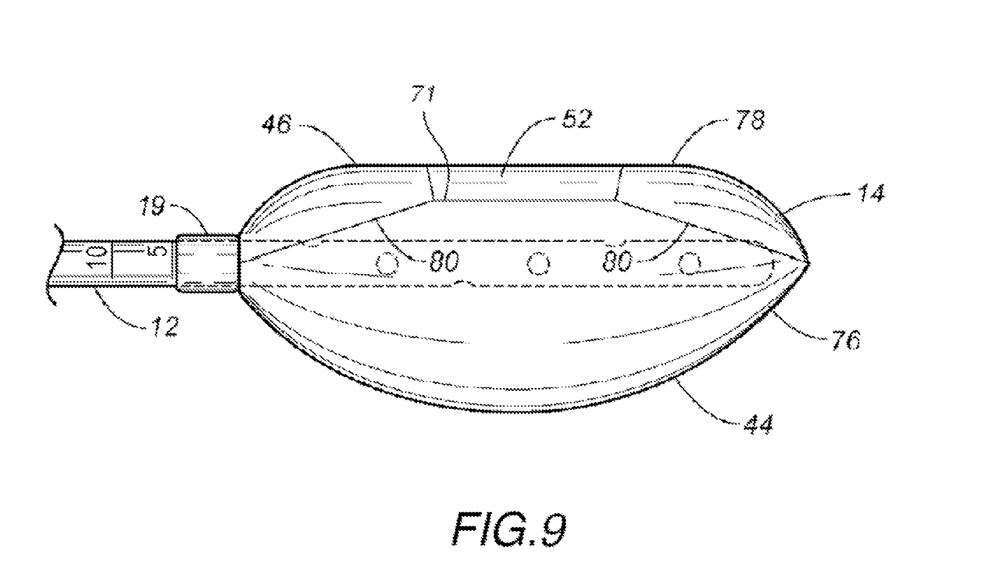
FIG. 9 is a cross-sectional side view of the balloon of the rectal balloon apparatus showing the plurality of layers that form the balloon, and groove formed by attaching the top surface to the middle layer.

FIG. 9 is a cross-sectional side view of the balloon 14, showing the plurality of layers that form the balloon 14. A bottom layer 76 forms the bottom portion 44 of the balloon 14. A top layer 78 forms the upper portion, including central seating area 46 and the groove 52, of the balloon 14. A middle layer 80 extends between the bottom layer 76 and the top layer 78. The middle layer 80 is connected to the top layer 78 at the groove 52.

As discussed above, the groove 52 at the central seating area 46 engages with the tip of the prostate to reduce the lateral movement of the balloon. To achieve that, however, it is important that the groove 52 maintains its shape even when the balloon 14 is subject to external pressure when put inside a patient's rectum. The groove 52 is thus formed by welding or otherwise attaching the top layer 78 with the middle layer 80 at the groove bottom 71. This way, a recessed or dimpled groove 52 with some depth can be maintained, thus its engagement with the patient's prostate, regardless of the external pressure that may or may not cause the remainder of the balloon to deform. A skilled artisan can understand that the bonding between the top layer 78 and the middle layer 80 at the groove bottom 71 can be achieved by other equivalent methods known in the field.

In general, the present invention assures uniformity and reproducibility of positioning. The stopper 13 provides an initial indication of the depth of positioning of the balloon 14. It is possible that the balloon 14 could have an improper rotational position in the rectum. A proper orientation of the balloon 14 is achieved by viewing the fiducial markers 72 by any imaging system. The lateral flatness of the balloon 14 is assuredly positioned against the prostate. In essence, the prostate is wedged by the inflated balloon into the dimple created by the groove 52, and is unable to slip from one side to the other as in the prior art non-conforming balloons. The sensor 70 is thereby properly positioned at the same location during all treatments. The sensor 70 can then be used to accurately determine the amount of radiation delivered during each external beam radiation treatment.

In use, the sensor cable is outfitted with adaptors for connection to the requisite radiation detector instrumentation, such as CCD camera, photodetector, photomultiplier tube, scintillation counter, MOSFET, vacuum photodetector, microchannel plates, and the like, which operably connects with a processor having the needed software to assess and report radiation dose. Using the rectal balloon with fiducial markers and sensor described herein, the radiologist can accurately position the balloon, wedge the prostate into the groove by inflation, and determine exactly where the device is using a variety of imaging means. Further, the radiologist can accurately measure radiation dose at multiple locations on the prostate, thus allowing further refinements in dosimetry.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

I claim:

1. A prostate immobilizing rectal balloon, said rectal balloon comprising:
   a. a flexible shaft having a fluid passageway extending therethrough and having a distal end and a proximal end,
   b. a balloon having an upper surface, a bottom surface, a distal end near said distal end of said shaft and a proximal end that is affixed to the proximal end of said shaft, such that said fluid passageway communicates with an interior of said balloon,
   c. wherein said balloon comprises a top layer connected to a bottom layer to form said balloon,
   d. said balloon further comprising a middle layer extending between said top layer and said bottom layer, wherein said middle layer is connected to said top layer to form a groove overlying said shaft and making said upper surface generally flattened as compared with said bottom surface,
   e. wherein said balloon has a non-inflated condition,
   f. wherein said balloon has an inflated condition, wherein said groove has depth and forms a central seating area that is configured to engage with a prostate, and
   g. said balloon further comprising i) a radiation sensor in said groove for determining radiation dose from an external beam radiation device, or ii) one or more fiducial markers, or iii) both of i) and ii).

2. The prostate immobilizing rectal balloon of claim 1, wherein a first plurality of fiducial markers are positioned on one side of said groove and a second plurality of fiducial markers are positioned on an opposite side of said groove.

3. The prostate immobilizing rectal balloon of claim 1, wherein said fiducial markers comprise a first set of fiducial markers positioned on said upper surface of said balloon and a second set of fiducial markers positioned on said bottom surface of said balloon.

4. The prostate immobilizing rectal balloon of claim 1, further comprising a stopping means comprising a semi-spherical member slidably mounted on said shaft, said semi-spherical member having a curved surface facing said balloon and a locking mechanism to lock said stopping means at a desired location on said shaft.

5. The prostate immobilizing rectal balloon of claim 1, wherein said radiation sensor has an outer surface that is flush with a surface of said balloon or inward of said surface of said balloon.

6. The prostate immobilizing rectal balloon of claim 1, said shaft further comprising indicia formed on an exterior surface thereof.

7. The prostate immobilizing rectal balloon of claim 1, said fiducial markers comprising tungsten.

8. The prostate immobilizing rectal balloon of claim 1, said shaft having a plurality of holes in fluid communication with said balloon, said holes offset from an adjacent hole.

9. A method of treating a prostate, comprising inserting a prostate immobilizing rectal balloon of claim 1 into a rectum of a patient, and inflating said balloon such that a prostate engages with said groove, confirming a position of said balloon via imaging said fiducial markers, treating said prostate with external beam radiation therapy and assessing a radiation dosage via said sensor.

\* \* \* \* \*